US010434048B2

(12) United States Patent
Dudley et al.

(10) Patent No.: US 10,434,048 B2
(45) Date of Patent: Oct. 8, 2019

(54) TOPICAL SUNSCREEN COMPOSITION, METHOD OF PREPARATION, AND USE THEREOF

(71) Applicant: CYBERDERM LABORATORIES INC., Ottawa (CA)

(72) Inventors: Denis Dudley, Ottawa (CA); Thomas Heinar, Toronto (CA); Sara Dudley, Toronto (CA)

(73) Assignee: CYBERDERM LABORATORIES INC., Ottawa (CA)

( * ) Notice: Subject to any disclaimer, the term of this patent is extended or adjusted under 35 U.S.C. 154(b) by 82 days.

(21) Appl. No.: 15/787,815

(22) Filed: Oct. 19, 2017

(65) Prior Publication Data

US 2018/0116923 A1 May 3, 2018

Related U.S. Application Data

(60) Provisional application No. 62/414,205, filed on Oct. 28, 2016.

(51) Int. Cl.

| | |
|---|---|
| ***A61Q 17/04*** | (2006.01) |
| ***A61K 8/27*** | (2006.01) |
| ***A61K 8/02*** | (2006.01) |
| ***A61K 8/19*** | (2006.01) |
| ***A61K 8/29*** | (2006.01) |
| ***A61K 8/49*** | (2006.01) |
| ***A61K 8/85*** | (2006.01) |

(52) U.S. Cl.

CPC .............. *A61K 8/27* (2013.01); *A61K 8/0241* (2013.01); *A61K 8/19* (2013.01); *A61K 8/29* (2013.01); *A61K 8/496* (2013.01); *A61K 8/4966* (2013.01); *A61K 8/85* (2013.01); *A61Q 17/04* (2013.01); *A61K 2800/412* (2013.01); *A61K 2800/413* (2013.01)

(58) Field of Classification Search

None

See application file for complete search history.

(56) References Cited

U.S. PATENT DOCUMENTS

| | | | | |
|---|---|---|---|---|
| 5,505,935 | A | 4/1996 | Guerrero et al. | |
| 7,153,494 | B2 | 12/2006 | Chodorowski-Kimmes et al. | |
| 2011/0142770 | A1 | 6/2011 | Fletcher et al. | |
| 2011/0287105 | A1* | 11/2011 | Gittleman .............. | A61K 8/046 424/501 |
| 2013/0071453 | A1 | 3/2013 | Sojka et al. | |
| 2015/0064224 | A1 | 3/2015 | Tong et al. | |
| 2015/0183928 | A1 | 7/2015 | Takezaki et al. | |
| 2015/0190320 | A1* | 7/2015 | Tachon .................... | A61K 8/29 424/401 |
| 2015/0209243 | A1 | 7/2015 | Shiroya et al. | |
| 2016/0067152 | A1* | 3/2016 | Franklin .............. | A61K 8/8147 424/401 |
| 2017/0119652 | A1 | 5/2017 | Doi et al. | |

FOREIGN PATENT DOCUMENTS

| | | | |
|---|---|---|---|
| CN | 105418944 | A | 3/2016 |
| EP | 2907501 | A1 | 8/2015 |
| WO | 2013/158844 | A2 | 10/2013 |
| WO | 2015/132792 | A1 | 9/2015 |
| WO | 2016/032852 | A1 | 3/2016 |

OTHER PUBLICATIONS

Database WPI, March 2016, Thomson Scientific, London, GB; AN 2016-210216, XP002775687, "Microsphere used for preparing cleaning care products and cosmetic, which is made of raw material that comprises biodegradable polymer, where bead is spherical bead".

Extended European Search Report dated Dec. 1, 2017, European patent application No. 17197688.9.

* cited by examiner

*Primary Examiner* — Susan T Tran

(74) *Attorney, Agent, or Firm* — Adrienne Bieber McNeil; ABM Intellectual Property Inc.

(57) ABSTRACT

A topical sunscreen composition includes metal oxide sunscreen particles, polylactic acid, and a cosmetic carrier in which the metal oxide sunscreen particles and polylactic acid are dispersed. A method of preparing a topical sunscreen composition includes dispersing metal oxide sunscreen particles and polylactic acid in a cosmetic carrier. A method of protecting human skin from ultraviolet (UV) radiation includes applying to human skin a topical sunscreen composition including metal oxide sunscreen particles and polylactic acid dispersed in a cosmetic carrier.

13 Claims, No Drawings

TOPICAL SUNSCREEN COMPOSITION, METHOD OF PREPARATION, AND USE THEREOF

CROSS-REFERENCES TO RELATED APPLICATIONS

This application claims the benefit of U.S. Provisional Patent Application No. 62/414,205, filed on Oct. 28, 2016, which is incorporated herein by reference in its entirety.

FIELD

This document relates to topical sunscreen compositions, methods of preparing topical sunscreen compositions, and uses of sunscreen compositions. More specifically, this document relates to topical sunscreen compositions that include metal oxide sunscreen particles.

BACKGROUND

US Patent Application Publication No. 2011/0142770 (Fletcher et al.) discloses sunscreen compositions comprising organic pigment particulates and methylcellulose. Also disclosed are methods of boosting the SPF (sun protection factor) and/or PPD (Persistent Pigment Darkening) of a sunscreen composition having organic pigment particulates. The methods involve including methylcellulose in the sunscreen composition.

U.S. Pat. No. 5,505,935 (Guerrero et al.) discloses a cosmetic sunscreen composition that includes an ethylene/vinyl acetate copolymer, an acrylic polymer such as poly (methyl methacrylate) and a chromophoric organic sunscreen agent capable of absorbing ultraviolet radiation within the range 290 to 400 nm. The ethylene/vinyl acetate copolymer and acrylic polymer were found to interactively boost the SPF value of the organic sunscreen.

SUMMARY

The following summary is intended to introduce the reader to various aspects of the detailed description, but not to define or delimit any invention.

According to some aspects, a topical sunscreen composition includes between about 1 wt % and about 35 wt % metal oxide sunscreen particles, between about 2.5 wt % and about 25 wt % polylactic acid, and a cosmetic carrier in which the metal oxide sunscreen particles and the polylactic acid are dispersed.

In some examples, the metal oxide sunscreen particles include at least one of titanium dioxide, iron oxide, zinc oxide, cerium dioxide, and zirconium dioxide. In some examples, the metal oxide sunscreen particles include at least one of titanium dioxide, zinc oxide, and cerium dioxide.

In some examples, the composition includes between about 2 wt % and about 25 wt % metal oxide sunscreen particles. In some examples, the composition includes between about 2 wt % and about 20 wt % metal oxide sunscreen particles. The metal oxide sunscreen particles can have an average metal oxide sunscreen particle diameter of between about 10 nm and about 1 micron.

In some examples, the composition includes between about 2.5 wt % and about 20 wt % polylactic acid. In some examples, the composition includes between about 5 wt % and about 15 wt % polylactic acid. The polylactic acid can be particulate polylactic acid. The particulate polylactic acid can have a polylactic acid particle diameter of between about 5 microns and about 20 microns.

In some examples, the cosmetic carrier includes at least one of a metal oxide sunscreen particle carrier, an emulsifier, an emulsifier substitute, a rheology modifier, water, a preservative, a film forming agent, an emollient and an additive.

In some examples, the composition further includes an organic UV absorbing agent. The organic UV absorbing agent can be a 1, 3, 5-triazine derivative, such as bis-ethylhexyloxyphenol methoxyphenyl triazine. Alternatively or in addition, the organic UV absorbing agent can include methylene bisbenzotriazolyl tetramethylbutylphenol. The composition can include between about 1 wt % and about 10 wt % methylene bis-benzotriazolyl tetramethylbutylphenol. The composition can include between about 0.1 wt % and about 10 wt % bis-ethylhexyloxyphenol methoxyphenyl triazine.

In some examples, the ultraviolet A (UV-A) protection factor of the composition is at least 13. In some examples, the UV-A protection factor of the composition is at least 21.

The composition can be a cream.

According to some aspects, a topical sunscreen composition includes metal oxide sunscreen particles, polylactic acid, and a cosmetic carrier in which the metal oxide sunscreen particles and polylactic acid are dispersed.

According to some aspects, a method of protecting human skin from ultraviolet (UV) radiation includes applying to human skin the sunscreen compositions as described above. The UV radiation can be UV-A radiation.

According to some aspects, a method of preparing a topical sunscreen composition includes a) dispersing metal oxide sunscreen particles and polylactic acid in a cosmetic carrier.

In some examples, step a) can include dispersing at least one of titanium dioxide, iron oxide, zinc oxide, cerium dioxide, and zirconium dioxide in the cosmetic carrier. In some examples, step a) includes dispersing at least one of titanium dioxide, zinc oxide, and cerium dioxide in the cosmetic carrier.

In some examples, step a) includes dispersing between about 1 wt % and about 35 wt % metal oxide sunscreen particles in the cosmetic carrier. In some examples, step a) includes dispersing between about 2.5 wt % and about 25 wt % metal oxide sunscreen particles in the cosmetic carrier.

In some examples, step a) includes dispersing metal oxide sunscreen particles have an average metal oxide sunscreen particle diameter of between about 10 nm and about 1 micron in the cosmetic carrier.

In some examples, step a) includes dispersing between about 2.5 wt % and about 20 wt % polylactic acid in the cosmetic carrier. In some examples, step a) can include dispersing between about 5 wt % and about 15 wt % polylactic acid in the cosmetic carrier.

In some examples, step a) can include dispersing particulate polylactic acid in the carrier. Step a) can include dispersing particulate polylactic acid having a polylactic acid particle diameter of between about 5 microns and about 20 microns in the cosmetic carrier.

In some examples, the cosmetic carrier includes at least one of a metal oxide sunscreen particle carrier, an emulsifier, an emulsifier substitute, a rheology modifier, water, a preservative, a film forming agent, an emollient and an additive.

In some examples, the method further includes dispersing an organic UV absorbing agent, such as a water or oil soluble organic UV absorbing agent, in the cosmetic carrier. The organic UV absorbing agent can be a 1, 3, 5-triazine derivative, such as bis-ethylhexyloxyphenol methoxyphenyl triazine. Alternatively or in addition, the organic UV absorbing agent can include methylene bisbenzotriazolyl tetramethylbutylphenol. In some examples, between about 1 wt % and about 10 wt % methylene bis-benzotriazolyl tetramethylbutylphenol is dispersed in the cosmetic carrier. In some examples, between about 0.1 wt % and about 10 wt % bis-ethylhexyloxyphenol methoxyphenyl triazine is dispersed in the cosmetic carrier.

DETAILED DESCRIPTION

Various compositions or processes will be described below to provide an example of an embodiment of the claimed subject matter. No embodiment described below limits any claim and any claim may cover processes or compositions that differ from those described below. The claims are not limited to compositions or processes having all of the features of any one composition or process described below or to features common to multiple or all of the compositions described below. It is possible that a composition or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Definitions

As used herein, the words “comprising” (and any form of comprising, such as “comprise” and “comprises”), “having” (and any form of having, such as “have” and “has”), “including” (and any form of including, such as “include” and “includes”) or “containing” (and any form of containing, such as “contain” and “contains”), are inclusive or open-ended and do not exclude additional, unrecited elements or process steps.

As used herein, the terms “about”, “substantially” and “approximately” mean a reasonable amount of deviation of the modified term such that the end result is not significantly changed. These terms of degree should be construed as including a deviation of at least ±5% of the modified term if this deviation would not negate the meaning of the word it modifies.

As used herein, the singular forms “a”, “an” and “the” can include plural references unless the content clearly dictates otherwise. For example, a composition including “a compound” can include one compound or two or more compounds.

As used herein, the term “and/or” means that the listed items are present or used individually or in combination. In effect, this term means that “at least one of” or “one or more” of the listed items is used or present.

As used herein, the term “particles”, for example as in “metal oxide sunscreen particles” or “polylactic acid particles”, refers to discrete localized quantities of matter. Particles may have a uniform or non-uniform size distribution. Particles may in some examples have an average particle size that is on the scale of nanometers or microns.

As used herein, the term “cosmetic carrier” refers to compositions or components that are suitable for use in contact with human skin without undue toxicity, incompatibility, instability, or allergic response.

As used herein, the term “oil soluble”, for example as in “oil soluble organic UV absorbing agent”, refers to a substance that has a solubility in oil based solutions that is sufficient for the substance to exert its desired effect.

As used herein, the term “water soluble”, for example as in “water soluble organic UV absorbing agent”, refers to a substance that has a solubility in water based solutions that is sufficient for the substance to exert its desired effect.

As used herein, the term “agent” indicates a compound or mixture of compounds that, when added to a composition, tend to produce a particular effect on the composition’s properties.

As used herein, the term “topical sunscreen composition” encompasses tanning lotions, sunscreens, and sunblocks which are intended for exterior bodily use to provide protection against UV rays. A topical sunscreen composition may, for example, be used to confer a health and/or cosmetic benefit to its user.

As used herein, the terms “wt %” or “weight %” or “weight percent” refer to the weight of an ingredient or agent divided by the total weight of the composition, multiplied by 100.

Compositions and Methods

Sunscreens including metal oxide sunscreen particles can protect skin from the UVB portion of sunlight through to the long wave portion of UVA sunlight. The particles can be relatively large, to deter the permeation of the particles into the skin.

Regulatory restrictions often limit the amount of metal oxide sunscreen particles in a composition. However, even when the amount of metal oxide sunscreen particles is maximized, there are theoretical limits to the UVA protection factor that can be achieved. For example, certain regulations limit the amount of zinc oxide in a composition to 25 wt %. The maximum theoretical UVA protection factor (in-silico, as determined by the BASF Sunscreen Simulator Tool) of zinc oxide at 25 wt % is 13.5. Similarly, certain regulations limit the amount of titanium dioxide in a composition to 10 wt %. The maximum theoretical UVA protection factor (in-silico, as determined by the BASF Sunscreen Simulator Tool) of titanium dioxide at 10 wt % is 6.7.

It has presently been determined that in topical sunscreen compositions that include metal oxide sunscreen particles, the UVA protection factor can be significantly increased by including polylactic acid (PLA) in the compositions. For example, as described in further detail below, in a given topical sunscreen composition that includes metal oxide sunscreen particles, the addition of PLA can increase the UVA protection factor by up to approximately 90%. Furthermore, it has presently been determined that in topical sunscreen compositions that include metal oxide sunscreen particles, the Sun Protection Factor, or SPF, can be significantly increased by including polylactic acid (PLA) in the compositions. Furthermore, it has presently been determined that in topical sunscreen compositions that include metal oxide sunscreen particles, the photostability can be significantly increased by including polylactic acid (PLA) in the compositions.

Accordingly, disclosed herein is a topical sunscreen composition that includes metal oxide sunscreen particles and polylactic acid, in a cosmetic carrier.

The metal oxide sunscreen particles can be or can include one or more of titanium dioxide, iron oxide, zinc oxide, cerium dioxide, zirconium dioxide, or other metal oxides that provide UV protection. In one particular example the metal oxide sunscreen particles include particles of zinc oxide, titanium dioxide, and cerium dioxide.

The topical sunscreen composition can include, for example, between about 1 wt % and about 35 wt % metal oxide sunscreen particles. In some examples, the topical sunscreen composition includes between about 2 wt % and about 25 wt % metal oxide sunscreen particles. In some examples, the topical sunscreen composition includes between about 2 wt % and about 20 wt % metal oxide sunscreen particles. In some examples, the topical sunscreen composition includes between about 5 wt % and about 18 wt % metal oxide sunscreen particles. In some examples, the topical sunscreen composition includes between about 10 wt % and about 18 wt % metal oxide sunscreen particles. In some examples, the topical sunscreen composition includes about 12 wt % zinc oxide particles, up to about 2.5 wt % titanium dioxide particles, and up to about 2.5% cerium dioxide particles. In other examples, the topical sunscreen composition includes about 18 wt % zinc oxide particles, up to about 2.5 wt % titanium dioxide particles, and up to about 2.5% cerium dioxide particles. In other examples, the topical sunscreen composition includes about 25 wt % zinc oxide particles, up to about 2.5 wt % titanium dioxide particles and up to about 2.5% cerium dioxide particles.

The majority of the metal oxide sunscreen particles can have, for example, a particle diameter (also referred to herein as a 'metal oxide sunscreen particle diameter') of between about 1 nm and about 1 micron. In some examples, the metal oxide sunscreen particles have an average particle diameter of between about 10 nm and about 1 micron. In some examples, the metal oxide sunscreen particles have an average particle diameter of between about 100 nm and about 1 micron.

The topical sunscreen composition can include, for example, up to 25 wt % polylactic acid. In some examples, the topical sunscreen composition includes between about 2.5 wt % and about 20 wt % polylactic acid. In some examples, the topical sunscreen composition includes between about 5 wt % and about 15 wt % polylactic acid. In some examples, the topical sunscreen composition includes about 5 wt % polylactic acid. In some examples, the topical sunscreen composition includes about 10 wt % polylactic acid. In some examples, the topical sunscreen composition includes about 15 wt % polylactic acid. In some examples, the topical sunscreen composition includes about 20 wt % polylactic acid.

In some examples, the polylactic acid is particulate. The particulate polylactic acid can have, for example, an average particle diameter (also referred to herein as a polylactic acid particle diameter) of between about 5 microns and about 20 microns. In some examples, the particulate polylactic acid has an average particle diameter of between about 6 microns and about 15 microns. In some examples, the particulate polylactic acid has a particle diameter of between about 8 microns and about 12 microns.

The particulate polylactic acid can have, for example, a density of between about 1 g/cc and about 1.5 g/cc, at 25 degrees Celsius. In some examples, the particulate polylactic acid has a density of between about 1.1 g/cc and about 1.4 g/cc, at 25 degrees Celsius. In some examples, the particulate polylactic acid has a density of between about 1.2 g/cc and about 1.3 g/cc, at 25 degrees Celsius.

The polylactic acid can have, for example, a melting point of between about 120 degrees Celsius and 170 degrees Celsius. In some examples, the polylactic acid has a melting point of between about 130 degrees Celsius and 160 degrees Celsius. In some examples, the polylactic acid has a melting point of between about 140 degrees Celsius and about 150 degrees Celsius.

The metal oxide sunscreen particles and polylactic acid can be dispersed in a cosmetic carrier. The cosmetic carrier can be a material or combination of materials that deliver the actives (i.e. metal oxide sunscreen particles and polylactic acid) to the skin. The cosmetic carrier can be selected to provide a topical sunscreen composition that is, for example, a lotion, a cream, a stick, a gel, a foam, or a spray, or combination thereof.

The cosmetic carrier can make up, for example, between 60 wt % and 90 wt % of the formulation. In some examples, the cosmetic carrier makes up between about 70 wt % and 80 wt % of the formulation. In some examples, the cosmetic carrier makes up about 75 wt % of the formulation.

The cosmetic carrier can in some examples include a metal oxide sunscreen particle carrier, and a bulk carrier.

The term "metal oxide sunscreen particle carrier" refers to a substance in which the metal oxide sunscreen particles are initially dispersed, and which is then combined with the other components of the topical sunscreen composition, including the bulk carrier. Examples of metal oxide sunscreen particle carriers include but are not limited to oils, solvents, esters or combinations thereof. In some examples, the metal oxide sunscreen carrier includes one or more of caprylic/capric triglycerides, medium chain triglycerides or esters, C12-15 Alkyl Benzoate, Jojoba esters, Neopentyl Glycol Diheptanoate, Coco Caprylate, Triethoxycaprylylsilane, Silica, Hydrogen Dimethicone, Isopropyl Titanium Triisostearate/Methicone Crosspolymer, Polyhydroxystearic Acid, Cyclopentasiloxane, Ethyl Trisiloxane, Isononyl Isononanoate, *Ricinus communis* (Castor) Seed Oil, and *Helianthus annuus* (Sunflower) Seed Oil.

The term "bulk carrier" refers to the components of the cosmetic carrier other than the metal oxide sunscreen particle carrier. The bulk carrier may be separately prepared, and then combined with the dispersion of the metal oxide sunscreen particles in the metal oxide sunscreen particle carrier.

The bulk carrier can include, but is not limited to, an emulsifier, an emulsifier substitute, a rheology modifier, water, a preservative, a film forming agent, an emollient, other additives or excipients, and combinations thereof.

An example of a suitable emulsifier is safflower oleosomes.

An example of an emulsifier substitute is a gelling agent for oils.

An example of a suitable rheology modifier is xanthan gum.

Examples of preservatives include caprylyl glycol, caprylhydroxamic acid, and/or glycerin.

Examples of a film forming agent include hydrogenated polycyclopentadiene and/or caprylic/capric triglyceride.

Examples of emollients are undecane and tridecane.

Examples of other additives and excipients include but are not limited to skin conditioning oils, oil absorbers, vitamins such as vitamin B3, fragrance, mineral oils, solvents, antioxidants, anti-inflammatory agents, moisturizers, humectants, and combinations thereof.

In some examples, the topical sunscreen composition includes one or more organic UV absorbing agents. The organic UV absorbing agent can include, for example, a 1, 3, 5-triazine derivative, such as bis-ethylhexyloxyphenol methoxyphenyl triazine. Alternatively or in addition, the organic UV absorbing agent can include a particulate organic filter such as methylene bisbenzotriazolyl tetramethylbutylphenol.

The topical sunscreen composition can include, for example, up to 15 wt % methylene bis-benzotriazolyl tetramethylbutylphenol. For example, the topical sunscreen composition can include between about 1 wt % and about 15 wt % methylene bis-benzotriazolyl tetramethylbutylphenol. In some examples, the topical sunscreen composition includes between about 5 wt % and about 10 wt % methylene bis-benzotriazolyl tetramethylbutylphenol. In some examples, the topical sunscreen composition includes about 8 wt % methylene bis-benzotriazolyl tetramethylbutylphenol.

The topical sunscreen composition can include, for example, up to 10 wt % bis-ethylhexyloxyphenol methoxyphenyl triazine. For example, the topical sunscreen composition can include between 0.1 wt % and about 10 wt % bis-ethylhexyloxyphenol methoxyphenyl triazine. In some examples, the topical sunscreen composition includes between about 0.5 wt % and about 5 wt % bis-ethylhexyloxyphenol methoxyphenyl triazine. In some examples, the topical sunscreen composition includes about 1 wt %, bis-ethylhexyloxyphenol methoxyphenyl triazine.

In some examples, the ultraviolet A (UV-A) protection factor of the composition is at least 13 (as measured using the revised Colipa in-vitro UVA method, described below). In some examples, the UV-A protection factor of the composition is at least 21. In some examples, the UV-A protection factor of the topical sunscreen composition is at least 33.

The topical sunscreen composition may be prepared, for example by dispersing the metal oxide sunscreen particles and polylactic acid in the cosmetic carrier. Any other ingredients, such as organic UV absorbing agents, may also be dispersed in the carrier.

In some examples, the metal oxide sunscreen particles are initially provided in a metal oxide sunscreen particle carrier, such as caprylic/capric triglycerides. For example, a dispersion of about 50 wt % metal oxide sunscreen particles and 50 wt % caprylic/capric triglycerides may be provided. This dispersion (also referred to as a metal oxide sunscreen particle dispersion), together with the polylactic acid, may be added to and dispersed in the bulk carrier. In some examples, the polylactic acid is the last ingredient added to the composition.

The metal oxide sunscreen particles and the polylactic acid may in some examples remain as discrete and separate particles in the cosmetic carrier. That is, in some examples, the metal oxide sunscreen particles and the polylactic acid generally do not aggregate, bond, coat or encapsulate each other, or otherwise combine.

The topical sunscreen composition may be used, for example, by applying the topical sunscreen composition to skin (e.g. human skin). The topical sunscreen composition can be used to protect the skin from UV radiation, and particularly UVA radiation.

EXAMPLES

Materials and Methods

Topical sunscreen compositions were prepared using the following components:

A. Polylactic Acid:

Particulate polylactic acid with a particle diameter of 8-12 microns, a melting point of 140-150 degrees Celsius, and a density at 25 degrees Celsius of 1.23-1.25 was used in amounts of 2.5 to 20 wt %, and at 0 wt % for control formulations.

B. Metal Oxide Sunscreen Particles:

(i) Zinc oxide with primary particles having a particle diameter of a few to several tens of nanometers, but with average particle size between 100 nm and 1 micron, was used. The zinc oxide was provided in caprylic/capric triglycerides (as a metal oxide sunscreen particle carrier), with up to 50 wt % zinc oxide per dispersion. Zinc oxide loading in the final topical sunscreen composition ranged from 12-25 wt %.

(ii) Titanium dioxide was provided in the rutile form and coated with alumina and stearic acid, with an average particle size of roughly 17 nm. Titanium dioxide loading in the final composition was up to 2.5 wt %.

(iii) Cerium dioxide was coated with silica and aluminum hydroxide. Cerium dioxide loading in the final composition was up to 2.5 wt %.

C. Organic UV Absorbing Agents (i) Bisoctrizole (commercial name Tinosorb M™, INCI name methylene bis-benzotriazolyl tetramethylbutylphenol) with a molecular weight of 659 Daltons was used. Bisoctrizole loading in the final topical sunscreen composition was 8 wt %.

(ii) Bemotrizinol (commercial name Tinosorb S™, INCI name bis-ethylhexyloxyphenol methoxyphenyl triazine) with a molecular weight of 628 Daltons. Bemotrizinol loading in the final topical sunscreen composition was 1 wt %.

D. Bulk Carrier

Three bulk carrier compositions were tested, bulk carrier (A), bulk carrier (B), and bulk carrier (C).

Bulk carrier (A) included safflower oleosomes (21 wt %), xanthan gum and other rheology modifiers (4 wt %), water (60 wt %), preservatives (caprylyl glycol, caprylhydroxamic acid, and glycerin) (2 wt %), skin conditioning oils and vitamin B3 (13 wt %), where the weight percent is expressed as a percentage of the total bulk carrier weight, and is approximate.

Bulk carrier (B) included a gelling agent for oils (52 wt %), a film forming agent (hydrogenated polycyclopentadiene and caprylic/capric triglyceride) (11 wt %), an emollient of undecane and tridecane (11%), preservatives (caprylyl glycol, caprylhydroxamic acid, and glycerin) (2 wt %), skin conditioning oils and vitamin B3 (24 wt %), where the weight percent is expressed as a percentage of the total bulk carrier weight, and is approximate.

Bulk Carrier (C) included safflower oleosomes (18%), skin conditioning oils (71%) and an anti-oxidant of norwegian spruce extract (11%), where the weight is expressed as a percentage of the total bulk carrier weight, and is approximate.

The topical sunscreen composition was prepared by adding the dispersion of zinc oxide particles in caprylic/capric triglycerides, the titanium dioxide particles, and the cerium oxide particles to the bulk carrier, and mixing to create a homogeneous composition. The polylactic acid was then added to the composition, and again the composition was mixed to create a homogenous composition.

The topical sunscreen compositions were tested in a third-party accredited laboratory using the revised Colipa in vitro UVA method as described in In Vitro Method for the Determination of the UVA Protection Factor and "Critical Wavelength" Values of Sunscreen Products—COLIPA Guideline (dated March 2011) using Labsphere's UV-2000S Benchtop Sunscreen Analyzer (S/N 1216135073). The long-arc xenon Atlas Suntest™ insolator, type CPS+, filtered with its original UV short cut-off filter (Ref: 56052388) combined with the "UV Special Glass" filter (Ref: 56052371), providing a VIS+UVA+UVB spectrum was used as UV source of the sunscreen sample irradiation. SunCool CPS/CPS+ Air Chiller (Ref: 56078923) was used for effective cooling of the samples. Treated PMMA plates were placed on a non-reflecting surface during UV exposure.

Each composition was applied to 3 HD-6 PMMA plates, and the absorbance spectrum was measured before and after irradiation with approximately 24 J/cm2. The initial SPF was calculated and the absorbance spectrum was adjusted by a constant, C, chosen to yield an SPF corresponding to an SPF value derived from pre-scan data, and the initial UVAPF (UVAPF0) was calculated from the adjusted absorbance spectrum, according to the Colipa Guideline for Determination of UVA Protection. The absorbance spectrum corresponding to a UVA dose of 1.2×UVAPF0 in J/cm, 2 was then determined and corrected by C, set to a value of 1, to obtain the UVAPF after irradiation. Photostability was calculated by comparing the UVA protection factor before and after irradiation, and is expressed as the % change in the UVAPF before and after irradiation.

The UVA Protection Factor (UFAPF) was determined for all compositions tested. SPF and photostability were determined only for compositions including Bulk Carrier (C).

Results:

Results are shown in Table 1.

The use of PLA increased the UVA protection factor whether organic UV absorbing agents were used or not, and in all bulk carriers.

It is believed that higher amounts of polylactic acid, such as up to 25% or greater, would result in an even further increased UVA protection factor, SPF, and photostability. It is also believed that similar results would be achieved with even higher amounts of metal oxide sunscreen particles.

Without being limited by theory, it is believed that the inclusion of Tinosorb S improved the dispersion of the metal oxide sunscreen particles, and therefore in the compositions that included Tinosorb S, less PLA was required to achieve an improvement in UVA protection.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

TABLE 1

UVA protection factor, SPF, and Photostability for topical sunscreen compositions including metal oxide sunscreen particles, with and without polylactic acid. Weight percent is expressed as a percentage of the weight of the final composition, unless otherwise indicated.

| Bulk Carrier | Metal Oxide Sunscreen Particles | Organic UV Absorbing Agents | Polylactic Acid | UVA Protection Factor | SPF | Photostability (% change in UVAPF) |
|---|---|---|---|---|---|---|
| Bulk Carrier (A) | 12 wt % Zinc Oxide | 8 wt % | 0 wt % | 21.6 | — | — |
| (to make 100 | (provided as dispersion in | Tinosorb M | 5 wt % | 33.66 | — | — |
| wt %) | capric/caprylic triglycerides, | 1 wt % | 15 wt % | 33.76 | — | — |
| | with up to 50 wt % zinc oxide | Tinosorb S | | | | |
| | in the dispersion) | | | | | |
| | up to 2.5% Titanium Dioxide | | | | | |
| | up to 2.5% Cerium Dioxide | | | | | |
| Bulk Carrier (B) | 18% Zinc Oxide | nil | 0 wt % | 11.08 | — | — |
| (to make 100 | (provided as dispersion in | | 5 wt % | 13.44 | — | — |
| wt %) | capric/caprylic triglycerides, | | 15 wt % | 21 | — | — |
| | with up to 50 wt % zinc oxide | | | | | |
| | in the dispersion) | | | | | |
| | up to 2.5% Titanium Dioxide | | | | | |
| | up to 2.5% Cerium dioxide | | | | | |
| Bulk Carrier (C) | 25% Zinc Oxide | nil | 0 wt % | 14.09 | 29 | 10.54 |
| (to make 100 | (provided as dispersion in | nil | 2.5 wt % | 14.14 | 30 | 5.05 |
| wt %) | capric/caprylic triglycerides, | nil | 5 wt % | 19.92 | 52 | 5.53 |
| | with up to 50 wt % zinc oxide | nil | 15 wt % | 18.71 | 53 | 6.39 |
| | in the dispersion) | nil | 20 wt % | 18.08 | 50 | 3.00 |
| | up to 2.5% Titanium Dioxide | | | | | |
| | up to 2.5% Cerium dioxide | | | | | |

Discussion:

The use of PLA resulted in an increased UVA protection factor for the topical sunscreen compositions. There was a maximum increase of 91%; however even at lower amounts of PLA (i.e. 2.5 wt % or 5% wt % PLA) the use of PLA improved the UVA protection factor.

The use of PLA resulted in an increased SPF for the topical sunscreen compositions. There was a maximum increase of 72%; however even at lower amounts of PLA (i.e. 2.5 wt % or 5% wt % PLA) the use of PLA improved the SPF.

The use of PLA resulted in an increased photostability for the topical sunscreen compositions. The percent change in UVAPF before and after irradiation decreased from 10.54% (with no PLA) to 3.00% with 20 wt % PLA.

The invention claimed is:

1. A topical sunscreen composition comprising:

i) between about 1 wt % and about 35 wt % metal oxide sunscreen particles;

ii) between about 2.5 wt % and about 25 wt % polylactic acid particles; and iii) a cosmetic carrier in which the metal oxide sunscreen particles and the polylactic acid particles are dispersed;

wherein the metal oxide sunscreen particles and the polylactic acid particles are discrete and separate particles;

wherein the polylactic acid particle have a diameter of between about 5 microns and about 20 microns; and wherein the sunscreen composition has an ultraviolet A (UV-A) protection factor of at least 13.

2. The composition of claim 1, wherein the metal oxide sunscreen particles comprise at least one of titanium dioxide, iron oxide, zinc oxide, cerium dioxide, and zirconium dioxide.

3. The composition of claim 1, wherein the composition comprises between about 2 wt % and about 25 wt % metal oxide sunscreen particles.

4. The composition of claim 1, wherein the composition comprises between about 2.5 wt % and about 20 wt % polylactic acid particles.

5. The composition of claim 1, wherein the composition comprises between about 5 wt % and about 15 wt % polylactic acid particles.

6. The composition of claim 1, wherein the cosmetic carrier comprises at least one of a metal oxide sunscreen particle carrier, an emulsifier, an emulsifier substitute, a rheology modifier, water, a preservative, a film forming agent, an emollient and an additive.

7. The composition of claim 1, further comprising an organic UV absorbing agent.

8. A method of protecting human skin from ultraviolet (UV) radiation, the method comprising applying to human skin a sunscreen composition comprising between about 1 wt % and about 35 wt % metal oxide sunscreen particles, between about 2.5 wt % and about 25 wt % polylactic acid particles, and a cosmetic carrier in which the metal oxide sunscreen particles and the polylactic acid particles are dispersed, wherein the metal oxide sunscreen particles and the polylactic acid particles are discrete and separate particles;

wherein the polylactic acid particle have a diameter of between about 5 microns and about 20 microns; and wherein the sunscreen composition has an ultraviolet A (UV-A) protection factor of at least 13.

9. A method of preparing a topical sunscreen composition, the method comprising:

a) dispersing between about 1 wt % and about 35 wt % metal oxide sunscreen particles and between about 2.5 wt % and about 25 wt % polylactic acid particles in a cosmetic carrier, and maintaining the metal oxide sunscreen particles and the polylactic acid particles as discrete and separate particles in the cosmetic carrier, wherein the metal oxide sunscreen particles and the polylactic acid particles are discrete and separate particles;

wherein the polylactic acid particle have a diameter of between about 5 microns and about 20 microns; and wherein the sunscreen composition has an ultraviolet A (UV-A) protection factor of at least 13.

10. The method of claim 9, wherein step a) comprises dispersing at least one of titanium dioxide, iron oxide, zinc oxide, cerium dioxide, and zirconium dioxide in the cosmetic carrier.

11. The method of claim 9, wherein the step a) comprises dispersing between about 5 wt % and about 15 wt % polylactic acid particles in the cosmetic carrier.

12. The method of claim 9 wherein the cosmetic carrier comprises at least one of a metal oxide sunscreen particle carrier, an emulsifier, an emulsifier substitute, a rheology modifier, water, a preservative, a film forming agent, an emollient and an additive.

13. The method of any one of claim 9, further comprising dispersing an organic UV absorbing agent in the cosmetic carrier.

* * * * *